United States Patent
Ramos

(10) Patent No.: US 6,673,836 B2
(45) Date of Patent: Jan. 6, 2004

(54) VEHICLE FOR APPLYING CHEMICAL COMPOUNDS ON WOOD

(76) Inventor: Rafael Rodriguez Ramos, Calle Linares, 7 Pta. 3, E-46018 Valencia (ES)

(*) Notice: Subject to any disclaimer, the term of this patent is extended or adjusted under 35 U.S.C. 154(b) by 0 days.

(21) Appl. No.: 10/371,740

(22) Filed: Feb. 21, 2003

(65) Prior Publication Data

US 2003/0162781 A1 Aug. 28, 2003

Related U.S. Application Data

(63) Continuation of application No. PCT/ES01/00175, filed on May 7, 2001.

(51) Int. Cl.$^7$ .................. A01N 43/40; A01N 43/56; A01N 47/28; A01N 31/14; A61K 31/22; A61K 31/695; A61K 31/66; A61K 31/41; A61K 31/415; A61K 31/215; A61K 31/235; A61K 31/135; A61K 31/075

(52) U.S. Cl. .................................................. 514/546

(58) Field of Search .................. 514/546, 63, 89, 514/132, 336, 383, 531, 532, 598, 646, 407, 721

(56) References Cited

FOREIGN PATENT DOCUMENTS

| EP | 0 537 447 B1 | 5/1995 |
|---|---|---|
| ES | 2 033 650 | 4/1993 |
| WO | WO 00/53017 A1 | 9/2000 |

*Primary Examiner*—Alton N. Pryor
(74) *Attorney, Agent, or Firm*—Akin, Gump, Strauss, Hauer & Feld, L.L.P.

(57) ABSTRACT

A vehicle for applying chemical compounds to wood comprises the following components in the indicated approximate percentages by weight of the total: toluene (40–70%), xylene (6–40%), benzophenone (3–18%), butyl glycol (2–9%), cetyl acetate (1–7%) and methanol (0.3–4%). The vehicle has a high wood penetration index and can be used for preparing compositions containing one or more chemical compounds useful for treating wood, for example insecticides and/or fungicides, for the purpose of treating or preventing damage caused by the attack of biological agents harmful for wood.

9 Claims, No Drawings

VEHICLE FOR APPLYING CHEMICAL COMPOUNDS ON WOOD

CROSS-REFERENCE TO RELATED APPLICATIONS

This application is a continuation of International Application No. PCT/ES01/00175, filed May 7, 2001, the disclosure of which is incorporated herein by reference.

BACKGROUND OF THE INVENTION

This invention is generally related to the treatment of woods by applying chemical compounds. The invention specifically refers to a vehicle that is useful for applying chemical compounds on wood.

Various harmful biological agents are known that are capable of attacking wood, causing significant damage. Among these biological agents harmful for wood are insects, for example beetles (a term which includes various species of wood-eating insects whose larvae gnaw and bore wood), termites, moths, etc., and fungi, for example *Poria vaillantii* Fr., Coniophora cerebella Duey, *Merulius lacrymans* Wulf, *Lentinus lepideus* Fr., *Lenzites sepiaria* Wulf, *Chaetomium globosum* Kunz, etc.

The products normally used for treating and conserving wood generally comprise one or more active substances that are effective against the harmful biological agents to be eliminated, for example one or more insecticides and/or fungicides, and a vehicle for introducing the active substances into the tunnels and cavities generated in the wood by the action of the harmful biological agents.

The number of vehicles that are effective as active substance carriers inside the wood is currently very limited. Among those vehicles normally used in products for treating and conserving wood are water, inorganic arsenic derivatives, pentachlorophenol and creosote.

Water is the most commonly used carrier. However, it scarcely penetrates the wood, so the active substances applied to the wood using the vehicle therefore do not satisfactorily penetrate it, remaining on the surface, thereby significantly reducing the effectiveness of the active substances.

The other vehicles have a very slight wood penetration index, generally about 2 to 6 mm after 24 hours. In soft and porous woods, penetration indices of the vehicle of up to 6 mm are obtained, whereas in hard and non-porous woods, the vehicles penetrate between 2 and 3 mm during a 24 hour time period.

Therefore, there is a necessity to find new vehicles that are useful for applying chemical compounds on woods, which vehicles advantageously have a high wood penetration index.

BRIEF SUMMARY OF THE INVENTION

The invention provides a solution to the existing necessity that comprises the development of a new vehicle for applying chemical compounds on woods, the vehicle comprising a mixture of several components. The vehicle has a high wood penetration index, determined by means of a trial comprising the application of the vehicle at a point on the wood, allowing the vehicle to act for a period of time, and determining the advance of the vehicle front by means of cutting the wood and measuring the advance of the vehicle front.

A vehicle such as the one provided by this invention is useful for treating woods, specifically for treating and preventing damage caused by the attack of biological agents that are harmful for wood.

One object of this invention is the vehicle for applying chemical compounds on woods. An additional object of this invention is a composition comprising the vehicle together with at least one chemical compound. Another object of this invention is a method for treating wood, comprising applying the composition in a sufficient quantity to the wood to be treated.

The invention provides a vehicle that is useful for applying chemical compounds on woods (hereinafter "vehicle of the invention"), the vehicle comprising:

| Components | Approx. percentage (%) by weight of the total |
|---|---|
| Toluene | 40–70 |
| Xylene | 6–40 |
| Benzophenone | 3–18 |
| Butyl glycol | 2–9 |
| Cetyl acetate | 1–7 |
| Methanol | 0.3–4 |
| | 100 |

All the components constituting the vehicle of the invention are commercial products. In the sense used in this description, the term "benzophenone" includes both benzophenone (diphenylmethanone) and the hydroxylated or methoxylated derivatives thereof (see for example *The Merck Index*, 11th Edition, (1989)). Likewise, the term "butyl" includes any of the butyl isomers.

In a particular embodiment, the vehicle of the invention has the following composition:

| Components | Approx. percentage (%) by weight of the total |
|---|---|
| Toluene | 64 |
| Xylene | 16 |
| Benzophenone | 10 |
| Butyl glycol | 5 |
| Cetyl acetate | 4 |
| Methanol | 1 |
| | 100 |

DETAILED DESCRIPTION OF THE INVENTION

The vehicle of the invention can be easily prepared by means of a process that comprises mixing the components in the desired proportions.

Several trials have clearly shown the high penetration index of the vehicle of the invention in different woods (see Example 1). It can therefore be used for applying chemical compounds on woods, for example, chemical compounds useful for treating woods, specifically for treating and preventing damage caused by the attack of biological agents that are harmful for wood (see Example 2).

The invention also provides a composition (hereinafter "composition of the invention"), the composition comprising at least one chemical compound and a vehicle of the invention. The vehicle of the invention can be present in the composition of the invention in a widely variable quantity; for example, the composition of the invention may contain about 0.1 to 99.9% by weight of the vehicle of the invention, the rest being constituted of the compound or chemical compounds, in which case the chemical compounds can be present in any weight ratio that is suitable among them. The composition of the invention can be easily obtained by mixing the vehicle of the invention with the compound or chemical compound in the suitable weight ratio. The composition of the invention is in liquid form, for example in a solution or dispersion.

In a particular embodiment of the invention, the composition of the invention is a composition that is useful for treating wood, comprising one or more chemical compounds that are useful for treating wood, in addition to the vehicle of the invention. In another more specific embodiment of the invention, the composition of the invention is an insecticide and/or fungicide composition, useful for treating and/or preventing damage caused by insects and/or fungi which attack wood, comprising one or more insecticides and/or one or more fungicides, in addition to the vehicle of the invention.

Among those insecticides and/or fungicides that may be present in the composition of the invention, the following examples are included: chlorpyrifos, fipronil, silafluofen, acetamiprid, etofenprox, tripropyl isocyanurate, fenobucarb, hexaflumuron, fenitrothion, esfenvalerate, imidacloprid, difluobenzuron, lambda-cyhalothrin, clothalonil, propiconazole and the mixtures thereof. In this case, the composition of the invention is useful for inhibiting the development of biological agents that are harmful for wood, such as insects, for example, beetles, termites, moths, etc., and fungi, for example, *Poria vaillantii* Fr., *Coniophora cerebella* Duey, *Merulius lacrymans* Wulf, *Lentinus lepideus* Fr., *Lenzites sepiaria* Wulf, *Chaetomium globosum* Kunz, etc.

The wood penetration index obtained with the composition of the invention generally corresponds to that of the vehicle used. The penetration index may vary, depending on the type of wood as well as the degree of humidity thereof.

The invention also provides a method for treating wood, which method comprises applying a composition of the invention to the wood to be treated in a sufficient quantity so as to obtain the desired effect. In the sense used in this description, the expression "applying a composition of the invention to the wood to be treated" includes, for example, applying the composition of the invention on the surface to the wood to be treated, as well as introducing the composition of the invention, by any suitable means, into the tunnels and cavities generated in the wood by the action, for example, of harmful biological agents.

The following examples serve to illustrate the invention and must not be considered limiting for the scope thereof.

EXAMPLE 1

Determination of the Wood Penetration Index of a Vehicle 1.1 Materials and Method The method used for determining the wood penetration index of a vehicle consists of applying a determined quantity of the vehicle to be tested (between 3 and 10 ml) at a point (origin) of the surface of the wood, allowing the vehicle to act for a determined time period (between 1–23 minutes), and measuring the advance of the vehicle front by means of cutting the wood and measuring the advance of the vehicle front inside the wood from the origin.

The woods used were representative of a broad spectrum of woods, from very soft and porous woods to very hard and non-porous woods. The woods that were specifically tested were the following: poplar, scots pine, walnut, cedar and beech wood. The woods were shaped into 20×7×7 cm pieces.

The vehicles tested were those whose compositions are described below. As the trials were being carried out and results were being obtained, the products were selected and those which resulted to be ineffective for the desired objective were discarded. Thus the composition of the vehicle of the invention was obtained.

I. Combinations of 2 Different Components:

1) Ethylene glycol/toluene
2) benzophenone-2/ethyl ether
3) disodium phosphate/monoxinol-9
4) butyl glycol/acetylene
5) methanol/benzol
6) dodecyl diamino ethyl/xylene
7) sodium sulphate/cetyl acetate
8) sodium hydroxide/methylene chloride For each combination, different concentrations were tested (in each case comprising 0.5 to 80% by weight of the total) of each one of the components present in each combination. The remainder up to 100% was composed of the other component.

II. Combinations of 3 Different Components:

1) cetyl acetate/sodium hydroxide/monoxinol-9
2) butyl glycol/ethyl ether/disodium phosphate
3) acetylene/dodecyl diamino ethyl/toluene
4) benzol/methylene chloride/sodium sulphate
5) benzophenone-2/acetylene/monoxinol-9
6) xylene/ethylene glycol/methanol For each combination, different concentrations were tested (in each case comprising 0.5 to 80% by weight of the total) of each one of the components present in each combination. The remainder up to 100% was composed of the other components.

III. Combinations of 4 Different Components:

1) ethyl ether/methanol/butyl glycol/sodium hydroxide
2) sodium sulphate/xylene/methylene chloride/benzol
3) dodecyl diamino ethyl/cetyl acetate/disodium phosphate/acetylene
4) benzophene-2/ethylene glycol/monoxinol-9/toluene
5) xylene/ethylene glycol/methanol For each combination, different concentrations were tested (in each case comprising 0.5 to 80% by weight of the total) of each one of the components present in each combination. The remainder up to 100% was composed of the other components.

IV. Combinations of 5 Different Components:

1) methanol/acetylene/ethylene glycol/benzol/disodium phosphate
2) xylene/methylene chloride/dodecyl diamino ethyl/sodium sulphate/monoxinol-9
3) benzophenone-2/sodium hydroxide/methanol/cetyl acetate/ethyl ether
4) acetylene/disodium sulphate/butyl glycol/methylene chloride/toluene For each combination, different concentrations were tested (in each case comprising 0.5 to 80% by weight of the total) of each one of the components present in each combination. The remainder up to 100% was composed of the other components.

V. Combinations of 6 Different Compounds:
1) toluene/ethyl ether/ethylene glycol/methanol/monoxinol-9/acetylene
2) sodium hydroxide/cetyl acetate/sodium sulphate/xylene/dodecyl diamino ethyl/benzol
3) benzophenone-2/methylene chloride/disodium phosphate/butyl glycol/acetylene/sodium hydroxide toluene/xylene/benzophenone-2/butyl glycol/cetyl acetate/methanol For each combination, different concentrations were tested (in each case comprising 0.5 to 80% by weight of the total) of each one of the components present in each combination. The remainder up to 100% was composed of the other components.

1.2 Results

In general, the best results, expressed as the measurement (in mm) of the advance of the vehicle front, were obtained with a vehicle whose composition contained 6 different components, specifically with a composition of type V.4 composed of toluene, xylene, benzophenone-2, butyl glycol, cetyl acetate and methanol. Specifically, with a vehicle having Composition A: 64% toluene, 16% xylene, 10% benzophenone-2, 5% butyl glycol, 4% cetyl acetate and 1% methanol, where all the percentages are by weight of the total, the results that were obtained are included in Table 1.

TABLE 1

Penetration index (PI) of composition A on different woods

| Wood | Quantity (ml) | Time (min) | PI (mm) |
|---|---|---|---|
| Poplar | 3 | 1 | 10 |
| Poplar | 6 | 2.5 | 15 |
| Poplar | 10 | 6 | 20 |
| Scots pine | 3 | 2 | 10 |
| Scots pine | 6 | 5 | 15 |
| Scots pine | 10 | 10 | 20 |
| Walnut | 3 | 6 | 10 |
| Walnut | 6 | 14 | 15 |
| Walnut | 10 | 20 | 20 |
| Cedar | 3 | 8 | 10 |
| Cedar | 6 | 17 | 15 |
| Cedar | 10 | 23 | 20 |
| Beech | 3 | 8 | 10 |
| Beech | 6 | 17 | 15 |
| Beech | 10 | 23 | 20 |

Further trials carried out with compositions containing one or more insecticides and/or fungicides together with a vehicle provided by this invention clearly showed that the penetration index of the composition was the same as that of the vehicle alone, i.e., without active substance(s).

EXAMPLE 2

Insecticide Composition and Effectiveness Trials

An insecticide composition was prepared, heretofore Composition B, which exhibited the following composition:

| | |
|---|---|
| Fenitrothion | 25% (total weight/volume) |
| Esfenvalerate | 2% (total weight/volume) |
| Vehicle* | remainder up to 100% |

*The vehicle composition was the following: 64% toluene, 16% xylene, 10% benzophenone-2, 5% butyl glycol, 4% cetyl acetate and 1% methanol, where all the rates are by weight with regard to the total weight (corresponding to Composition A in Example 1).

The density of the insecticide composition was 0.9 g/ml.

The insecticide composition was obtained by adding fenitrothion and esfenvalerate, in suitable amounts, to the vehicle obtained previously by mixing its components in the suitable amounts.

In order to evaluate the effectiveness of the insecticide composition (Composition B), which contained a vehicle provided by this invention, the following trials were carried out:

2.1 Determination of the preventive effectiveness against termites; and 2.2 Determination of the threshold of preventive effectiveness against termites 2.1 Determination of the Preventive Effectiveness Against Termites 2.1.1 Brushing 2.1.1.1 Materials and Methods The tested insecticide composition is Composition B. No solvent was used to dissolve the insecticide composition. Pure gelatin was used for clogging up to the heads of the test tubes, as indicated by the standard.

The biological material used was *Reticulitermes lucifugus* Rossi.

The trial standard was UNE standard 56411:1992 (Una Norma Española—A Spanish Standard) (EN 118:1990) "Wood protectors. Determination of preventive effectiveness against *Reticulitermes santonensis* of Feytaud. Laboratory method."

The trial was carried out on wood test tubes obtained from *Pinus sylvestris* L. originating from the Valsaín mountain, in accordance with the requirements of the standard.

The minimum dose obtained by means of treatment by brushing, as indicated by the standard, was 43.05 ml/m$^2$.

2.1.1.2 Treatment

On the Mar. 10, 2000, the minimum possible amount of insecticide composition (43.05 ml/m$^2$), with a tolerance of ±5%, was applied by brushing on one of the sides of the test tube, checking by weighing that the desired amount had been applied, thus obtaining the insecticide composition absorptions and retentions that are included in Table 2.

After treatment, the test specimens were left to dry and were treated in an air conditioned chamber at a temperature of 20±2° C. and a relative humidity of 65±5% for 7 weeks, prior to putting them in contact with the insect colonies. The termite colonies were put in contact with the test tube using a polyurethane foam on the May 3, 2000, and the test apparatuses were placed in a chamber at a temperature of 27±2° C. and a relative humidity of 75±5% for 8 weeks.

The final examination was carried out on the Jun. 26, 2000. The attacks of the test tubes were evaluated as per the following scale:

0: No sign of attack
1: Tentative attack
2: Light attack
3: Medium attack
4: Strong attack The results obtained are included in Table 2.

TABLE 2

Preventive effectiveness against termites (UNE 56411:1992)
Unaged test tubes. Brushed

| Test specimen number | Tested doses Theoretical doses | | Tested doses Applied Doses | | Examination results Survival | | Degree of attack |
|---|---|---|---|---|---|---|---|
| | $g/m^2$ | $ml/m^2$ | $g/m^2$ | $ml/m^2$ | O (%) | S and N (n) | (0–4) |
| 1 | 12.0– | 13.33– | 38.75 | 43.05 | 0 | 0—0 | 0 |
| 3 | 15.0 | 16.66 | 38.75 | 43.05 | 0 | 0—0 | 0 |
| 4 | | | 38.75 | 43.05 | 3 | 0—0 | 0 |
| 5 | | | 38.75 | 43.05 | 1 | 0—0 | 0 |
| 7 | | | 40.00 | 44.44 | 0 | 0—0 | 0 |
| 9 | | | 40.00 | 44.44 | 2 | 0—0 | 0 |
| T1 | Untreated | | — | — | 91 | 0—2 | 4 |
| T2 | samples | | — | — | 96 | 1—2 | 4 |
| T3 | | | — | — | 97 | 1—3 | 4 |

[O: workers; S: soldiers; N: nymphs; n: number]

The results obtained clearly show that the tested insecticide composition (Composition B) is effective against termites for surface treatments by a method providing a dose of approximately 43 ml/m² on the wood that is actually treated. To evaluate the possibility that the effectiveness threshold is below the tested dose (43 ml/m²), several trials were carried out using a treatment method based on spraying the insecticide composition on the wood to be treated.

2.1.2 Spraying

2.1.2.1 Materials and Methods

The tested insecticide composition is Composition B. No solvent was used to dissolve the insecticide composition. Pure gelatin was used for clogging up to the heads of the test tubes, as indicated by the standard.

The biological material used was *Reticulitermes lucifugus* Rossi (the termite species conventionally existing in Spain).

The trial standard was the UNE standard 56411:1992 (EN 118:1990) "Wood protectors. Determination of preventive efficacy against Reticulitermes santonensis of Feytaud. Laboratory method."

The trial was carried out on wood test specimen obtained from *Pinus sylvestris* L. originating from the Burgui mountain (Navarra), in accordance with the requirements of the standard.

The tested insecticide composition concentrations were the following: 13.33 ml/m² and 16.66 ml/m². The insecticide composition was applied by means of spraying.

2.1.2.2 Treatment

On the Jun. 20, 2000, the indicated doses of insecticide composition, with a tolerance of ±5%, were applied by spraying on one of the sides of the test specimen, checking by means of weighing that the desired amounts had been applied, thus obtaining the insecticide composition absorptions and retentions that are included in Tables 3 and 4.

After treatment, the test tubes were left to dry and were treated in an air conditioned chamber at a temperature of 20±2° C. and a relative humidity of 65±5% for 10 weeks prior to putting them in contact with the insect colonies or aging them.

In order to age the test tubes, the latter were subjected to an aging trial by evaporation for 12 weeks, as per the methodology indicated in the UNE standard 56406:1992 [Wood protectors. Accelerated aging trials of treated woods prior to biological trials. Evaporation test].

The termite colonies were put in contact with the test specimen using a polyurethane foam on the Jul. 27, 2000 (for the unaged test specimen) and on the Oct. 30, 2000 (for the test specimen subjected to aging by evaporation), and the test devices were placed in a chamber at a temperature of 27±2° C. and a relative humidity of 75±5% for 8 weeks.

The final examination was carried out on the Oct. 24, 2000 (for the unaged test specimen) and on the Jan. 2, 2001 (for the test specimen subjected to aging by evaporation). The attacks of the test specimen were evaluated as per the following scale:

0: No sign of attack
1: Tentative attack
2: Light attack
3: Medium attack
4: Strong attack The results obtained are included in Tables 3 and 4.

TABLE 3

Preventive effectiveness against termites (UNE 56411:1992)
Unaged test specimen. Spraying

| Test specimen number | Tested doses Theoretical doses | | Tested doses Applied Doses | | Examination results Survival | | Degree of attack |
|---|---|---|---|---|---|---|---|
| | $g/m^2$ | $ml/m^2$ | $g/m^2$ | $ml/m^2$ | O (%) | S and N (n) | (0–4) |
| 1 | 12.0– | 13.33– | 16.16 | 17.95 | 0 | 0—0 | 0 |
| 3 | 15.0 | 16.66 | 14.98 | 16.64 | 0 | 0—0 | 0 |
| 4 | | | 15.05 | 16.72 | 0 | 0—0 | 0 |
| 5 | | | 13.75 | 15.27 | 0 | 0—0 | 0 |
| 7 | | | 16.33 | 18.14 | 0 | 0—0 | 0 |
| 9 | | | 15.03 | 16.70 | 0 | 0—0 | 0 |
| TA | Untreated | | — | — | 83 | 1—1 | 4 |
| TB | samples | | — | — | 86 | 2—1 | 4 |
| TB' | | | — | — | 87 | 1—1 | 4 |

[O: workers; S: soldiers; N: nymphs; n: number]

TABLE 4

Preventive efficacy against termites (UNE 56411:1992)
Aged test specimen (EN 73). Spraying

| Test specimen number | Tested doses Theoretical doses | | Tested doses Applied Doses | | Examination results Survival | | Degree of attack |
|---|---|---|---|---|---|---|---|
| | $g/m^2$ | $ml/m^2$ | $g/m^2$ | $ml/m^2$ | O (%) | S and N (n) | (0–4) |
| 1' | 12.0– | 13.33– | 16.16 | 17.95 | 0 | 0—0 | 0 |
| 3' | 15.0 | 16.66 | 14.98 | 16.64 | 0 | 0—0 | 0 |
| 4' | | | 15.05 | 16.72 | 0 | 0—0 | 0 |
| 5' | | | 13.75 | 15.27 | 0 | 0—0 | 0 |
| 7' | | | 16.33 | 18.14 | 0 | 0—0 | 0 |
| 9' | | | 15.03 | 16.70 | 0 | 0—0 | 0 |
| TA' | Untreated | | — | — | 94 | 2—1 | 4 |
| TB' | samples | | — | — | 86 | 3—2 | 4 |
| TB | | | — | — | 91 | 2—1 | 4 |

[O: workers; S: soldiers; N: nymphs; n: number]

The results obtained clearly show that the tested insecticide composition (Composition B) is effective against termites for surface treatments by a method providing a dose of 13.33 to 16.66 ml/m² on the wood that is actually treated. Given that the product has shown to be effective at the lowest dose of 13.33 ml/m², it is likely that it is effective at doses that are lower than those specified.

2.2 Determination of the Threshold of Preventive Effectiveness Against Termites

2.2.1 Materials and Method

The tested insecticide composition is Composition B.

The biological material used was *R. lucifugus* Rossi (the termite species normally existing in Spain).

The trial standard was the UNE standard 56410:1992 (EN 117:1990) "Wood protectors. Determination of the threshold of preventive efficacy against *Reticulitermes santonensis* of Feytaud. Laboratory method."

The trial was carried out on wood test specimen obtained from *Pinus sylvestris* L. originating from the Burgui mountain (Navarra), in accordance with the requirements of the standard.

To dilute the insecticide composition, xylene was used. The tested concentrations were the following: 0%, 0.01%, 0.023%, 0.045%, 0.065% and 0.085%.

2.2.2 Treatment

On the Jun. 16, 2000, the impregnation of the test specimen was carried out by atmospheric pressure vacuum, as indicated by the standard, thus obtaining the insecticide composition absorptions and retentions that are included in Tables 5 and 6.

After treatment, the test specimen were left to dry and were treated in an air conditioned chamber at a temperature of 20±2° C. and a relative humidity of 65±5% for 6 weeks prior to putting them in contact with the insect colonies or aging them.

To age the test specimen, once the latter are treated, they are subjected to an aging trial by evaporation for 12 weeks, as per the methodology indicated in the UNE standard 56406:1992.

The termite colonies were put in contact with the test specimen by using a polyurethane foam on the Jul. 27, 2000 (for the unaged test specimen) and on the Oct. 30, 2000 (for the test specimen subjected to aging by evaporation), and the test devices were placed in a chamber at a temperature of 27±2° C. and a relative humidity of 75±5% for 8 weeks.

The final examination was carried out on the Sep. 18, 2000 for the unaged test specimen and on the Jan. 2, 2001 for the test specimen subjected to aging by evaporation. The attacks of the specimen were evaluated as per the following scale:

0: No sign of attack
1: Tentative attack
2: Light attack
3: Medium attack
4: Strong attack The results obtained are included in Tables 5 and 6. These results clearly show that the tested insecticide composition (Composition B) is effective against termites for deep treatments by a process providing a retention of approximately 0.04 kg/m³ on the wood that is actually impregnated. Given that the product has proven to be effective at the lowest dose (0.01%), it is likely that the effectiveness threshold is below the specified retention.

TABLE 5

Threshold of preventive efficacy against termites (UNE 56410:1992)
Unaged test specimen

| Tested concentrations (%) | Test specimen no. | Solution discharge $(m_1 - m_0)$ (g) | Product retention | | Visual examination (0–4) | Surviving termites | | |
|---|---|---|---|---|---|---|---|---|
| | | | Test specimen (kg/m³) | Mean (kg/m³) | | O (%) | S (n) | N (n) |
| Xylene (0) | $X_2$ | 7.65 | 0 | 0.00 | 4 | 228 | 2 | 1 |
| | $X_3$ | 8.01 | 0 | | 4 | 226 | 1 | 2 |
| | $X_8$ | 7.93 | 0 | | 4 | 231 | 1 | 2 |
| 0.01 | 1 | 7.33 | 0.04 | 0.04 | 1 | 0 | 0 | 0 |
| | 2 | 7.27 | 0.04 | | 1 | 1 | 0 | 1 |
| | 6 | 7.24 | 0.04 | | 0 | 5 | 0 | 1 |
| 0.023 | 13 | 8.23 | 0.10 | 0.10 | 1 | 0 | 0 | 0 |
| | 14 | 7.80 | 0.10 | | 1 | 0 | 0 | 1 |
| | 17 | 7.93 | 0.10 | | 0 | 0 | 0 | 0 |
| 0.045 | 33 | 7.38 | 0.18 | 0.18 | 1 | 0 | 0 | 0 |
| | 34 | 7.68 | 0.18 | | 1 | 0 | 0 | 0 |
| | 36 | 7.48 | 0.18 | | 1 | 0 | 0 | 0 |
| 0.064 | 38 | 8.05 | 0.27 | 0.28 | 1 | 0 | 0 | 0 |
| | 39 | 8.01 | 0.27 | | 1 | 0 | 0 | 1 |
| | 40 | 8.41 | 0.29 | | 1 | 0 | 0 | 0 |
| 0.085 | 49 | 9.41 | 0.42 | 0.42 | 1 | 0 | 0 | 0 |
| | 50 | 9.45 | 0.42 | | 0 | 0 | 0 | 0 |
| | 51 | 9.46 | 0.42 | | 1 | 0 | 0 | 0 |
| Test solutions | T1 | — | — | — | 4 | 239 | 2 | 1 |
| | T2 | — | — | — | 4 | 226 | 1 | 1 |
| | T3 | — | — | — | 4 | 232 | 2 | 2 |

[O: Workers; S: Soldiers; N: Nymphs; n: number]

TABLE 6

Threshold of preventive effectiveness against termites (UNE 56410:1992)
Aged test specimen (EN 73)

| Tested concentrations (%) | Test specimen no. | Solution charge (m1 − m0) (g) | Product retention Test specimen (kg/m³) | Product retention Measurement (kg/m³) | Visual examination (0–4) | Surviving termites O (%) | Surviving termites S (n) | Surviving termites N (n) |
|---|---|---|---|---|---|---|---|---|
| Xylene (0) | X₁ | 7.22 | 0 | 0.00 | 4 | 195 | 1 | 2 |
|  | X₁₀ | 8.02 | 0 |  | 4 | 210 | 0 | 3 |
|  | X₁₂ | 7.56 | 0 |  | 4 | 219 | 0 | 3 |
| 0.01 | 7 | 7.33 | 0.04 | 0.04 | 0 | 0 | 0 | 0 |
|  | 8 | 7.64 | 0.04 |  | 0 | 0 | 0 | 0 |
|  | 9 | 7.51 | 0.04 |  | 0 | 1 | 0 | 2 |
| 0.023 | 19 | 8.09 | 0.10 | 0.10 | 0 | 0 | 0 | 0 |
|  | 22 | 7.76 | 0.10 |  | 0 | 0 | 0 | 2 |
|  | 23 | 7.26 | 0.09 |  | 0 | 0 | 0 | 0 |
| 0.045 | 26 | 7.70 | 0.19 | 0.19 | 0 | 0 | 0 | 0 |
|  | 27 | 7.84 | 0.20 |  | 1 | 0 | 0 | 0 |
|  | 32 | 7.59 | 0.19 |  | 0 | 0 | 0 | 0 |
| 0.064 | 38 | 8.07 | 0.28 | 0.28 | 1 | 0 | 0 | 0 |
|  | 39 | 7.90 | 0.27 |  | 0 | 0 | 0 | 1 |
|  | 40 | 8.22 | 0.28 |  | 1 | 0 | 0 | 0 |
| 0.085 | 49 | 9.34 | 0.42 | 0.42 | 1 | 0 | 0 | 0 |
|  | 51 | 9.37 | 0.42 |  | 1 | 0 | 0 | 0 |
|  | 52 | 9.35 | 0.42 |  | 0 | 0 | 0 | 0 |
| Test solutions | T1 | — | — | — | 4 | 95 | 1 | 3 |
|  | T2 | — | — | — | 4 | 88 | 2 | 2 |
|  | T3 | — | — | — | 4 | 89 | 1 | 3 |

[O: Workers; S: Soldiers; N: Nymphs; n: number]

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A vehicle useful for applying a chemical compound on wood, the vehicle comprising a mixture of the following components:

| Component | Approx. percentage (%) by weight of the total |
|---|---|
| Toluene | 40–70 |
| Xylene | 6–40 |
| Benzophenone | 3–18 |
| Butyl glycol | 2–9 |
| Cetyl acetate | 1–7 |
| Methanol | 0.3–4 |
|  | 100. |

2. The vehicle according to claim 1, wherein the mixture comprises:

| Component | Approx. percentage (%) by weight of the total |
|---|---|
| Toluene | 64 |
| Xylene | 16 |
| Benzophenone | 10 |
| Butyl glycol | 5 |
| Cetyl acetate | 4 |
| Methanol | 1 |
|  | 100. |

3. A composition comprising the vehicle according to claim 1 and at least one chemical compound.

4. The composition according to claim 3, wherein the at least one chemical compound is selected from the group consisting of insecticides and fungicides.

5. The composition according to claim 4, wherein the at least one chemical compound is selected from the group consisting of chlorpyrifos, fipronil, silafluofen, acetamiprid, etofenprox, tripropyl isocianurate, fenobucarb, hexaflumuron, fenitrothion, esfenvalerate, imidacloprid, difluobenzuron, lambda-cyhalothrin, clothalonil, and propiconazole.

6. A method for treating wood, comprising applying a composition according to claim 3 to the wood to be treated.

7. The method according to claim 6, wherein the wood to be treated is subject to damage caused by biological agents harmful for wood.

8. The method according to claim 7, wherein the composition comprises at least one chemical compound selected from the group consisting of insecticides and fungicides.

9. The method according to claim 7, wherein the composition comprises at least one chemical compound selected from the group consisting of chlorpyrifos, fipronil, silafluofen, acetamiprid, etofenprox, tripropyl isocianurate, fenobucarb, hexaflumuron, fenitrothion, esfenvalerate, imidacloprid, difluobenzuron, lambda-cyhalothrin, clothalonil, and propiconazole.

* * * * *